(12) United States Patent
Galluzzi

(10) Patent No.: US 11,826,482 B2
(45) Date of Patent: Nov. 28, 2023

(54) ASSEMBLY FOR THE SANITATION OF THE TERMINALS OF WASTEWATER DISCHARGING PIPES

(71) Applicant: STAIES S.R.L., Ciciliano (IT)

(72) Inventor: Andrea Galluzzi, Ciciliano (IT)

(73) Assignee: Staies S.r.l., Ciciliano (IT)

(*) Notice: Subject to any disclaimer, the term of this patent is extended or adjusted under 35 U.S.C. 154(b) by 736 days.

(21) Appl. No.: 16/975,281

(22) PCT Filed: Feb. 22, 2019

(86) PCT No.: PCT/IT2019/050036
§ 371 (c)(1),
(2) Date: Aug. 24, 2020

(87) PCT Pub. No.: WO2019/162977
PCT Pub. Date: Aug. 29, 2019

(65) Prior Publication Data
US 2021/0369886 A1  Dec. 2, 2021

(30) Foreign Application Priority Data
Feb. 26, 2018 (IT) .......... 102018000003045

(51) Int. Cl.
*A61L 2/10* (2006.01)
*E03F 1/00* (2006.01)
*B61D 35/00* (2006.01)

(52) U.S. Cl.
CPC .............. *A61L 2/10* (2013.01); *B61D 35/007* (2013.01); *A61L 2202/11* (2013.01);
(Continued)

(58) Field of Classification Search
CPC .... A61L 2/10; A61L 2202/11; A61L 2202/16; A61L 2202/17; B61D 35/007; E03F 1/008
See application file for complete search history.

(56) References Cited

U.S. PATENT DOCUMENTS

2017/0284076 A1  10/2017 Jensen
2018/0051447 A1  2/2018 Hills et al.

FOREIGN PATENT DOCUMENTS

DE          4102760 A1    8/1992
WO    2004011038 A1    2/2004
(Continued)

OTHER PUBLICATIONS

International Search Report in corresponding International Patent Application No. PCT/IT2019/050036, dated Mar. 6, 2019, 4 pages.
(Continued)

*Primary Examiner* — Sean M Luck
(74) *Attorney, Agent, or Firm* — FisherBroyles, LLP; Robert Kinberg

(57) ABSTRACT

A sanitation assembly for sanitation of terminals of wastewater discharging pipes includes a sanitation chamber inside which, while in use, there is located a terminal to be sanitized. A fixed UV emission means is located inside the sanitation chamber near a bottom portion thereof and arranged to emit a UV radiation upwards, the fixed UV emission means including a first plurality of LEDs arranged along a first circumference and a second plurality of LEDs arranged along a second circumference inside said first circumference, the first and the second plurality of LEDs being arranged to emit upward a UV radiation having a wavelength ranging from 200 and 300 nm. A movable UV emission means is housed inside the sanitation chamber and includes a third plurality of LEDs designed to emit a radiation ranging from 200 and 300 nm and arranged along a circumference on a vertically moving ring-shaped structure which, while in use, is arranged to surround the terminal to be subject to sanitation. The LEDs of the third plurality of LEDs are designed to emit, in a converging manner, a UV
(Continued)

radiation having the wavelength ranging from 200 to 300 nm.

7 Claims, 3 Drawing Sheets

(52) U.S. Cl.
CPC ....... *A61L 2202/16* (2013.01); *A61L 2202/17* (2013.01); *E03F 1/008* (2013.01)

(56) References Cited

FOREIGN PATENT DOCUMENTS

| WO | 2013172953 A1 | 11/2013 |
| WO | 2014171886 A1 | 10/2014 |
| WO | 2016001776 A1 | 1/2016 |
| WO | 2017207494 A1 | 12/2017 |

OTHER PUBLICATIONS

Italian Search Report in corresponding Italian Patent Application No. 201800003045, date of completion Oct. 24, 2018, 10 pages with English Translation.

ASSEMBLY FOR THE SANITATION OF THE TERMINALS OF WASTEWATER DISCHARGING PIPES

CROSS-REFERENCE TO RELATED APPLICATIONS

This application is a U.S. National Stage of International Patent Application No. PCT/IT2019/050036 filed on Feb. 22, 2019, which claims benefit of Italian Patent Application No. 102018000003045, filed Feb. 26, 2018.

FIELD OF THE INVENTION

The present invention relates to an assembly for the sanitation of the terminals of wastewater discharging pipes. More specifically, the present invention is aimed to the discharge of the wastewater from the train toilets, to which the description will make explicit reference without losing its generality.

BACKGROUND

As it is known to the specialists of the sector, the collection reservoirs of wastewater from train toilets are periodically subjected to a series of necessary unloading and sanitation operations.

These operations take place through a centralized system or by single machines positioned along the track near the train.

Generally, these operations involve at least (a) the suction of wastewater and the discharge of the same from the sealed retreat of the carriage to the sewage system; (b) the injection at a high pressure of a disinfectant solution in the sealed retreat of the carriage; and (c) the clear water load in a storage tank of the carriage.

Despite the above operations are almost always carried out automatically, it is always requested direct human intervention, nevertheless. As it may seem evident to a specialist of the branch, such intervention necessarily involves an element of risk of biological contamination for the personnel in charge. Such circumstance, that occurs, in particular, with the contact between the operator and the pipe connection terminal wastewater suction, which must be withdrawn manually by the operator and placed inside a special housing compartment at the end of its use.

Until now, this problem has been addressed from the industry sector almost exclusively by providing the use of protective devices supplied to the staff handling the terminal.

For a more complete understanding of the problem above, it should be considered that the connection terminal of the wastewater suction pipe can represent a contaminating element not only for operators but also for the other circuits connected to the toilet, such as the clear water charging circuit in a carriage storage tank.

Therefore, the need was felt to have one sanitizing device for an effective sanitation of the connection terminals for the suction pipe of the wastewater from the toilets.

SUMMARY

An object of the present invention is to provide a sanitation assembly for the sanitation of the terminals of wastewater discharging pipes.

The above and other objects are achieved, in one embodiment, by a sanitation assembly for sanitation of terminals of wastewater discharging pipes, comprising: a sanitation chamber which houses, in use, a terminal to be subjected to sanitation; fixed UV emission means housed inside the sanitation chamber close to a bottom portion thereof and are arranged to emit a UV radiation upwards, the fixed UV emission means comprising a first plurality of LEDs arranged along a first circumference, and a second plurality of LEDs arranged along a second circumference arranged inside said first circumference, said first and said second plurality of LEDs being arranged to emit upwards a UV radiation having a wavelength ranging from 200 to 300 nm; and movable UV emission means housed inside the sanitation chamber and comprising a third plurality of LEDs designed to emit a radiation having a wavelength ranging from 200 to 30 nm and arranged along a circumference on a vertically movable ring-shaped structure which, in use, is arranged to surround the terminal to be subjected to sanitation; the LEDs of the third plurality of LEDs being designed to emit, in a converging manner, the UV radiation having a wavelength ranging from 200 to 300 nm.

DESCRIPTION OF THE DRAWINGS

Below, there is a purely illustrative and non-limiting example of embodiment with the help of attached figures, in which.

DETAILED DESCRIPTION

Figure 1:
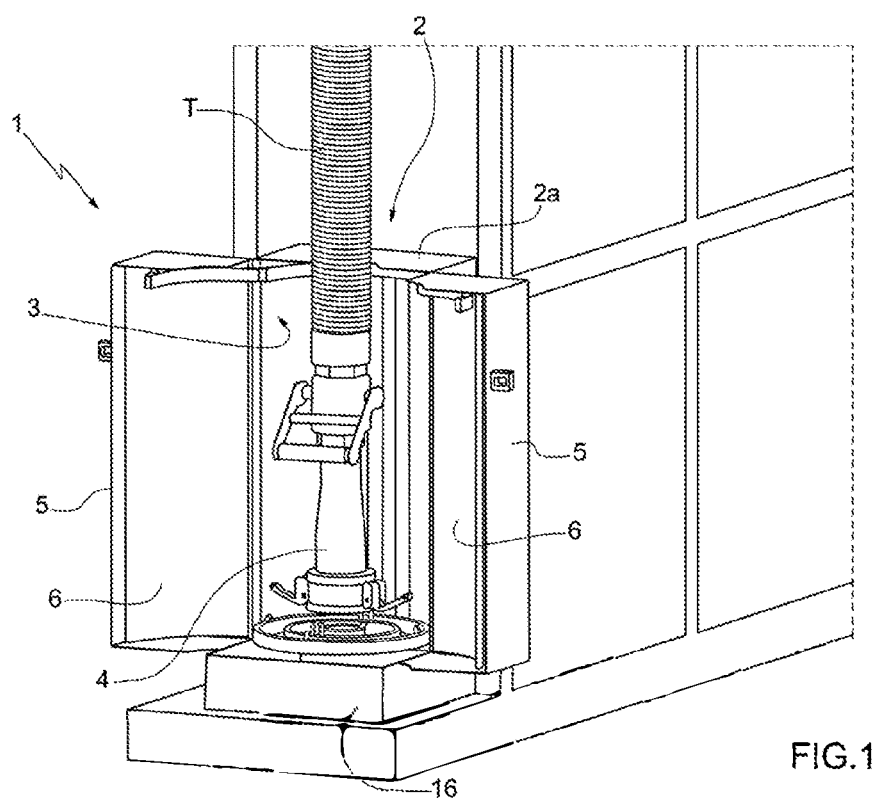
FIG. 1 is a perspective view of the assembly for the sanitation.

FIG. 1 shows a sanitation assembly 1 according to the present invention.

Sanitation assembly 1 comprises a containment structure 2 defining internally a sanitation chamber 3 suitable to house a terminal 4 for the connection of the aspiration pipe of wastewater from the toilets.

The containment structure 2 comprises a pair of doors 5 which, once closed, define a wall front, part of an upper wall 2a and part of side walls of the containment structure 2. In particular, in the upper wall 2a there is a hole adapted to house the suction pipe T to which the terminal 4 is connected.

The side walls, the front wall and the posterior wall of the containing chamber 2 carry internally a respective a curve side wall 6 such as achieve, once the containing chamber 2 is closed, a single cylindrical lateral surface of the sanitation chamber 3. Each of the cylindrical side wall 6 is covered with a reflective layer in such a way as to make the sanitation chamber completely defined by a single reflective cylindrical surface.

Figure 2:
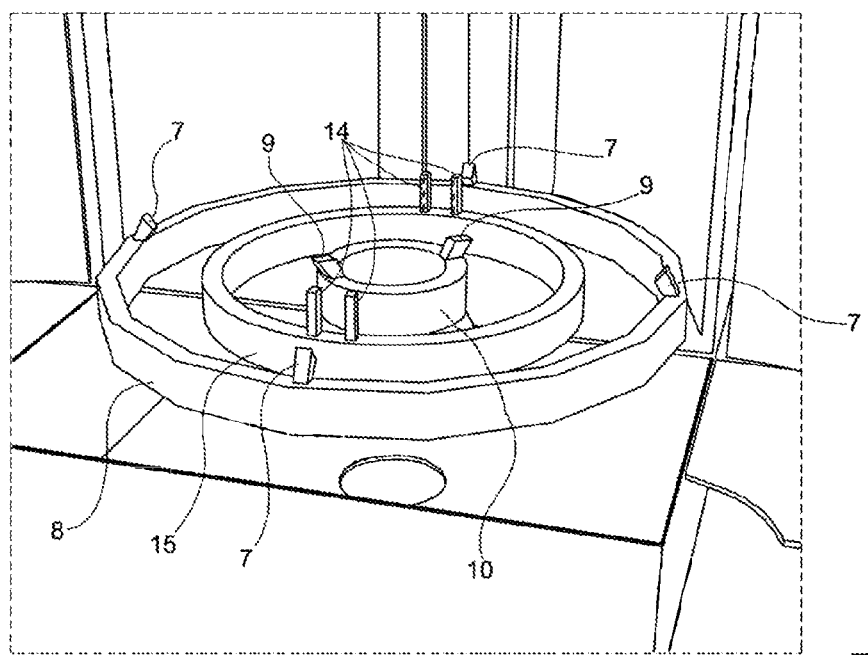
FIG. 2 shows an enlarged view of a detail of the assembly for the sanitation of FIG. 1.

As better illustrated in FIG. 2, the assembly 1 includes fixed UV emission means composed of one first plurality of LEDs 7 fixed at regular intervals to a first substantially circular structure 8 arranged on a bottom wall of the containing chamber 2, and a second plurality of LEDs 9 also fixed at regular intervals to a second circular structure 10 substantially arranged coplanar, internally and coaxial with the first circular structure 8.

In particular, the first plurality of LEDs 7 includes four LEDs and the second plurality of LEDs 9 includes two LEDs. Preferably, according to the present invention, the first plurality of LEDs 7 includes a number comprised between three and eight thereof, while the second plurality of LEDs 9 includes a number between two and four thereof.

LEDs from both the first 7 and the second 9 plurality, are arranged to direct the UV radiation upwards in order to hit, in this way, from the bottom both the interior and the exterior of the terminal 4 with the UV radiation itself.

Figure 3:
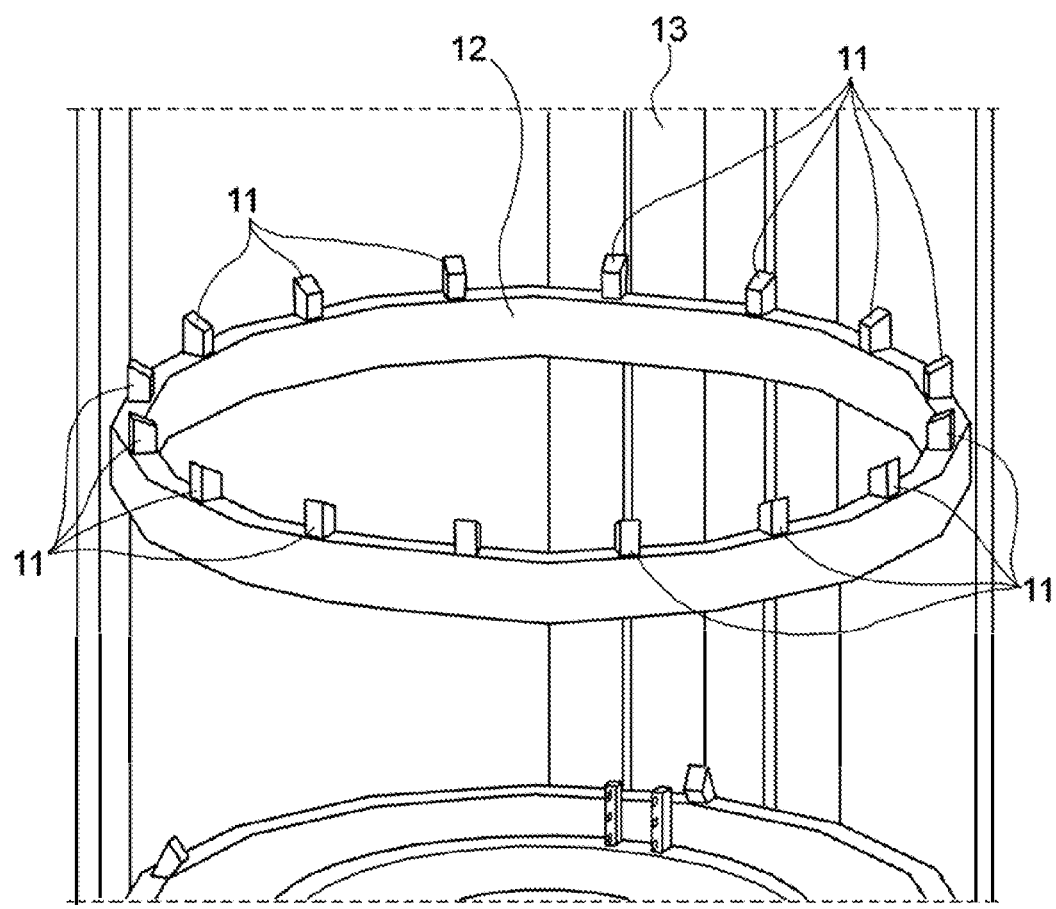
FIG. 3 shows an enlarged view of another element of the assembly for the sanitation of FIG. 1.

As better illustrated in FIG. 3, the assembly 1 includes mobile UV emission means composed of a third plurality of LEDs 11 fixed at regular intervals to a third substantially circular structure 12 arranged to move vertically along fixed vertical tracks 13 fixed to the rear wall of the containing chamber 2. LEDs of this third plurality 11 are arranged to address UV radiation in a concentric way.

In particular, the third plurality of LEDs 11 includes sixteen LEDs and, preferably, according to the present invention includes a number between twelve and twenty.

In use, the third circular structure 12 is arranged to surround the terminal 4 in such a way that by moving vertically, the LEDs 11 are able to hit with the UV radiation all the external wall of the terminal 4. Moreover, the third circular structure 12 is coaxial and parallel with the first 8 and the second 10 circular structure.

LEDs of the first 7, second 9 and third plurality 11 emit at a wavelength equal to 254 nm. Preferably, according to the present invention, the LEDs emit at a wavelength between 200 and 300 nm.

As better illustrated in FIG. 2 the assembly 1 includes irrigation means composed of four nozzles 14 obtained in a circular structure 15 arranged between the first circular structure 8 and the second structure circular 10, to which it is coplanar and coaxial.

The four nozzles 14 are made to direct their own jet of disinfectant solution upwards in such a way to hit the terminal 4 from below. The assembly 1 comprises a collection tank 16 arranged to collect the wastewater and the solution disinfectant from the terminal 4.

In use, once the suction/discharge procedure of toilet waste is terminated, the doors 5 of the containing chamber 2 will open and the terminal 4 is housed inside the sanitation chamber. With the subsequent closing of the doors 5, the suction pipe T to which the terminal 4 is connected is located inside the hole that is created in the upper wall 2a that is formed.

At this point, first the nozzles 14 are activated to hit the terminal 4 with a disinfectant solution from below and then the LEDs are activated. All this procedure will last the necessary time to insure with a reasonable certainty the sanitation of the terminal 4.

Finally, the assembly 1 object of the present invention can include a control unit to be able to activate remotely the nozzles and the LEDs.

The base of the present invention is the intuition of applying the UV technology to the sanitation of plants pipe terminals responsible for the suction of wastewater. In this way, you can get a safer use from the operator and prevent the contamination of other possible circuits, such as, for example, in the case of the CET, those responsible for the loading of clear water to fill the flushes on board.

The invention described above, in addition to being able to be adapted to the equipment for the discharge of train toilets, can find advantageous application also in other sectors, such as for example centralized systems, carnages unloading vents, outlets of self-discharge, camper toilets, etc.

Finally, it should be emphasized how the arrangement of the LEDs in the assembly of the present invention allows to guarantee the sanitation of the terminals regardless of their particular conformation.

The invention claimed is:

1. A sanitation assembly for sanitation of terminals of wastewater discharging pipes, comprising:
a sanitation chamber which houses, in use, a terminal to be subjected to sanitation;
fixed UV emission means housed inside the sanitation chamber close to a bottom portion thereof and are arranged to emit a UV radiation upwards, said fixed UV emission means comprising a first plurality of LEDs arranged along a first circumference, and a second plurality of LEDs arranged along a second circumference arranged inside said first circumference, said first and said second plurality of LEDs being arranged to emit upwards a UV radiation having a wavelength ranging from 200 to 300 nm; and
movable UV emission means housed inside the sanitation chamber and comprising a third plurality of LEDs designed to emit a radiation having a wavelength ranging from 200 to 30 nm and arranged along a circumference on a vertically movable ring-shaped structure which, in use, is arranged to surround said terminal to be subjected to sanitation, said LEDs of said third plurality of LEDs being designed to emit, in a converging manner, the UV radiation having a wavelength ranging from 200 to 300 nm.

2. The sanitation assembly according to claim 1, wherein said first plurality of LEDs, said second plurality of LEDs and said third plurality of LEDs are arranged along respective circumferences, which are coaxial to one another.

3. The sanitation assembly according to claim 1, wherein said first plurality of LEDs comprises a number of LEDs ranging from 3 to 8, said second plurality of LEDs comprises a number of LEDs ranging from 2 to 4, and said third plurality of LEDs comprises a number of LEDs ranging from 12 to 20.

4. The sanitation assembly according to claim 1, wherein the LEDs of said first, said second and said third plurality of LEDs emit a radiation having a wavelength ranging from 250 to 280 nm.

5. The sanitation assembly according to claim 1, wherein said sanitation chamber comprises a cylindrical side wall having a reflecting inner surface.

6. The sanitation assembly according to claim 1, further comprising pre-washing means comprising a plurality of nozzles housed inside the sanitation chamber close to a bottom portion thereof and arranged to emit a high-pressure pre-washing solution upwards, and a discharge system in a bottom portion of said sanitation chamber.

7. The sanitation assembly according to claim 1, further comprising a containing chamber defining, on the inside, said sanitation chamber and comprising a pair of doors which, once closed, define a front wall, part of an upper wall and part of side walls of the containing structure, the upper wall including a hole to house a suction pipe to which the terminal is connected.

* * * * *